United States Patent
Jang et al.

(10) Patent No.: US 9,737,240 B2
(45) Date of Patent: Aug. 22, 2017

(54) APPARATUS AND METHOD FOR RECOGNIZING GAIT MOTION

(71) Applicant: Samsung Electronics Co., Ltd., Suwon-Si, Gyeonggi-Do (KR)

(72) Inventors: Jun-Won Jang, Seoul (KR); Kyung-Rock Kim, Yongin-si (KR); Youngbo Shim, Seoul (KR); Jusuk Lee, Hwaseong-si (KR); Bokman Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 59 days.

(21) Appl. No.: 14/556,841

(22) Filed: Dec. 1, 2014

(65) Prior Publication Data

US 2016/0029928 A1    Feb. 4, 2016

(30) Foreign Application Priority Data

Jul. 29, 2014    (KR) .......................... 10-2014-0096320

(51) Int. Cl.
| | |
|---|---|
| *A61B 5/11* | (2006.01) |
| *A61B 5/00* | (2006.01) |
| *A63B 24/00* | (2006.01) |
| *A61H 3/00* | (2006.01) |

(Continued)

(52) U.S. Cl.
CPC ............ *A61B 5/112* (2013.01); *A61B 5/1122* (2013.01); *A61H 1/0244* (2013.01); *A61H 3/00* (2013.01); *G07C 1/22* (2013.01); *A61B 5/7264* (2013.01); *A61H 2201/165* (2013.01); *A61H 2201/5058* (2013.01); *A61H 2201/5061* (2013.01);

(Continued)

(58) Field of Classification Search
CPC ...................................................... A61B 5/112
See application file for complete search history.

(56) References Cited

U.S. PATENT DOCUMENTS

| | | | |
|---|---|---|---|
| 6,360,597 | B1 | 3/2002 | Hubbard, Jr. |
| 9,188,963 | B2 | 11/2015 | Gray et al. |
| 9,204,797 | B2 | 12/2015 | Gray et al. |

(Continued)

FOREIGN PATENT DOCUMENTS

| | | | |
|---|---|---|---|
| KR | 101053491 B1 | 8/2011 | |
| KR | 101317354 B1 | 10/2013 | |

(Continued)

OTHER PUBLICATIONS

Martínez-Solís, Fermín, et al. "Design of a low cost measurement system based on accelerometers for gait analysis." Acta Scientiarum. Technology 36.1 (2014): 111-121.*

(Continued)

*Primary Examiner* — Michael C Stout
*Assistant Examiner* — Nicholas E Kolderman
(74) *Attorney, Agent, or Firm* — Harness, Dickey & Pierce P.L.C.

(57) ABSTRACT

An apparatus and method for recognizing a gait motion by detecting a landing point in time of a foot of a user based on sensed acceleration information, inferring a gait motion based on right and left hip joint angle information of the user sensed at the detected landing point in time of the foot of the user, and detecting a landing leg between both legs of the user based on the inferred gait motion may be provided.

15 Claims, 9 Drawing Sheets

(51) Int. Cl.
*A61H 1/02* (2006.01)
*G07C 1/22* (2006.01)

(52) U.S. Cl.
CPC .............. *A61H 2201/5069* (2013.01); *A61H 2201/5079* (2013.01); *A61H 2201/5084* (2013.01)

(56) References Cited

U.S. PATENT DOCUMENTS

| | | |
|---|---|---|
| 9,451,881 B2 | 9/2016 | Gray et al. |
| 2010/0324699 A1 | 12/2010 | Herr et al. |
| 2011/0295384 A1 | 12/2011 | Herr et al. |
| 2012/0089330 A1 | 4/2012 | Hesch et al. |
| 2012/0215140 A1 | 8/2012 | Hirata et al. |
| 2013/0296746 A1 | 11/2013 | Herr et al. |
| 2014/0121575 A1* | 5/2014 | Yasuhara .................. A61H 3/00 601/35 |
| 2016/0107309 A1* | 4/2016 | Walsh .................... B25J 9/0006 248/550 |

FOREIGN PATENT DOCUMENTS

| | | |
|---|---|---|
| KR | 101358943 B1 | 2/2014 |
| KR | 101361362 B1 | 2/2014 |

OTHER PUBLICATIONS

Ng, Sau Kuen, and Howard Jay Chizeck. "Fuzzy model identification for classification of gait events in paraplegics." Fuzzy Systems, IEEE Transactions on 5.4 (1997): 536-544.*

Yamakawa, Takeshi, "Biometric Personal Identification Based on Gait Pattern Using Both Feet Pressure Change".

Huang, Bufu, "Gait Modeling for Human Identification". *2007 IEEE International Conference on Robotics and Automation*, (Apr. 2007), pp. 4833-4838, Italy.

Gafurov, Davrondzhon "Biometric Gait Authentication Using Accelerometer Sensor" *Journal of Computers*, (Oct./ Nov. 2006), p. 51-59, vol. 1. No. 7.

Kong, Kyoungchul, "A Gait Monitoring System Based on Air Pressure Sensors Embedded in a Shoe" (2009), p. 358-370. vol. 14, No. 3.

* cited by examiner

APPARATUS AND METHOD FOR RECOGNIZING GAIT MOTION

CROSS-REFERENCE TO RELATED APPLICATION

This application claims priority under 35 U.S.C. §119 to Korean Patent Application No. 10-2014-0096320, filed on Jul. 29, 2014, in the Korean Intellectual Property Office, the disclosure of which is incorporated herein by reference in its entirety.

BACKGROUND

1. Field

Example embodiments relate to apparatuses and/or methods for recognizing a gait motion, and more particularly, to apparatuses and/or methods for recognizing a gait motion based on biometric data of a user sensed by, for example, a walking assistance apparatus.

2. Description of the Related Art

Human walking is performed using different operating mechanisms of hip joints for level walking, walking in an upward inclined direction, for example, walking up stairs, and walking in a downward inclined direction, for example, walking down stairs.

When a walking assistance apparatus is unable to recognize a gait motion of a user during assisting walking of the user, the walking assistance apparatus may assist walking by, for example, collectively generating an oscillator-based pattern for each gait motion. However, such a walking assistance apparatus may not provide a walking assistance.

Thus, when human walking is to be assisted by, for example, a walking assistance apparatus, it is desired to recognize a gait motion of a user. The walking assistance apparatus may operate differently, using operating mechanisms, with respect to recognized gait motions, respectively, thereby providing an optimized walking assistance.

SUMMARY

At least one example embodiment relates to an apparatus for recognizing a gait motion.

According to an example embodiment, an apparatus for recognizing a gait motion includes a gait motion inference unit configured to infer a gait motion based on right and left hip joint angle information of a user, the right and left hip joint angle information sensed at a point in time at which a foot of the user lands, and a landing leg detector configured to detect a landing leg between both legs of the user based on the inferred gait motion.

According to some example embodiments, the right and left hip joint angle information may include at least one of angles of a right hip joint and a left hip joint, a difference between the angles of the right hip joint and the left hip joint, and motion directions of the right hip joint and the left hip joint.

According to some example embodiments, the gait motion may include a level walking motion, a walking motion in an upward inclined direction, a walking motion in a downward inclined direction, and a standing motion.

According to some example embodiments, the apparatus may further include a landing point in time detector configured to detect a landing point in time of a foot of the user based on sensed acceleration information.

According to some example embodiments provide that the landing point in time detector may be configured to detect a prediction horizon as the landing point in time when a difference between a mean acceleration for a base horizon set based on a previous step duration horizon and a mean acceleration for the prediction horizon is greater than or equal to a threshold value.

According to some example embodiments, the base horizon may be set to follow a freeze horizon preset from a previous landing point in time to prevent or mitigate an error in detection of the landing point in time.

According to some example embodiments, the landing point in time detector may be configured to detect the landing point in time of the foot of the user by shifting the prediction horizon when the difference between the mean acceleration for the base horizon and the mean acceleration for the prediction horizon is less than the threshold value.

According to some example embodiments, the mean acceleration for the base horizon may be updated for each step or preset to a first acceleration.

According to some example embodiments provide that the gait motion inference unit may be configured to infer the gait motion using a fuzzy logic. The gait motion inference unit may be configured to infer the gait motion by performing defuzzification based on a desired (or alternatively, preset) fuzzy rule and a value obtained by fuzzification of the right and left hip joint angle information using a membership function, and the membership function may be set based on the right and left hip joint angle information.

According to some example embodiments, the landing leg detector may be configured to detect, as the landing leg, a leg having a greater hip joint angle between angles of the right hip joint and the left hip joint included in the right and left hip joint angle information when the inferred gait motion corresponds to a level walking motion or a walking motion in an upward inclined direction.

According to some example embodiments provide that the landing leg detector may be configured to detect, as the landing leg, a leg having a motion direction with a negative velocity between motion directions of the right hip joint and the left hip joint included in the right and left hip joint angle information when the inferred gait motion corresponds to a walking motion in a downward inclined direction.

At least one example embodiment relates to a walking assistance apparatus.

According to an example embodiment, a walking assistance apparatus includes a driving portion configured to drive a right hip joint and a left hip joint of a user, a sensor portion configured to sense right and left hip joint angle information, an inertial measurement unit (IMU) sensor configured to sense acceleration information in response to walking of the user, and a controller configured to control the driving portion by inferring a gait motion of the user based on the right and left hip joint angle information, the right and left hip joint angle information sensed at a landing point in time of a foot of the user, the landing point in time detected based on the acceleration information, and detect a landing leg based on the inferred gait motion.

According to some example embodiments, the controller may include a landing point in time detector configured to detect the landing point in time of the foot of the user based on the sensed acceleration information, a gait motion inference unit configured to infer the gait motion based on the right and left hip joint angle information of the user sensed at the detected landing point in time, and a landing leg detector configured to detect the landing leg between both legs of the user based on the inferred gait motion.

According to some example embodiments, the landing point in time detector may be further configured to detect a prediction horizon as the landing point in time when a difference between a mean acceleration for a base horizon set based on a previous step duration horizon and a mean acceleration for the prediction horizon is greater than or equal to a threshold value.

According to some example embodiments, the gait motion inference unit may be configured to infer the gait motion using a fuzzy logic.

According to some example embodiments, the landing leg detector may be configured to detect, as the landing leg, a leg having a greater hip joint angle between angles of the right hip joint and the left hip joint included in the right and left hip joint angle information when the inferred gait motion corresponds to a level walking motion or a walking motion in an upward inclined direction, and to detect, as the landing leg, a leg having a motion direction with a negative velocity between motion directions of the right hip joint and the left hip joint included in the right and left hip joint angle information when the inferred gait motion corresponds to a walking motion in a downward inclined direction.

At least one example embodiment relates to a method of recognizing a gait motion.

According to an example embodiment, a method of recognizing a gait motion includes inferring a gait motion based on right and left hip joint angle information of a user sensed at a landing point in time of a foot of the user, and detecting a landing leg between both legs of the user based on the inferred gait motion.

According to some example embodiments, the method may further include detecting the landing point in time of the foot of the user based on sensed acceleration information.

According to some example embodiments, the detecting a landing point in time may include detecting a prediction horizon as the landing point in time when a difference between a mean acceleration for a base horizon set based on a previous step duration horizon and a mean acceleration for the prediction horizon is greater than or equal to a threshold value.

According to some example embodiments, the inferring may include inferring the gait motion using a fuzzy logic, and inferring the gait motion by performing defuzzification based on a desired (or alternatively, preset) fuzzy rule and a value obtained by fuzzification of the right and left hip joint angle information using a membership function. The membership function may be set based on the right and left hip joint angle information.

According to some example embodiments, the detecting a landing leg may include detecting, as the landing leg, a leg having a greater hip joint angle between angles of a right hip joint and a left hip joint included in the right and left hip joint angle information when the inferred gait motion corresponds to a level walking motion or a walking motion in an upward inclined direction, and detecting, as the landing leg, a leg having a motion direction with a negative velocity between motion directions of the right hip joint and the left hip joint included in the right and left hip joint angle information when the inferred gait motion corresponds to a walking motion in a downward inclined direction.

At least one example embodiment relates to an operating method of a walking assistance apparatus.

According to an example embodiment, an operating method of a walking assistance apparatus includes determining a gait motion based on sensed right and left hip joint angle information of a user, and outputting a driving control signal to drive a right hip joint and a left hip joint of the user based on the determined gait motion.

According to some example embodiments, the method may further include detecting a landing leg between a right leg and a left leg of the user based on the gait motion.

Additional aspects of example embodiments will be set forth in part in the description which follows and, in part, will be apparent from the description, or may be learned by practice of the disclosure.

BRIEF DESCRIPTION OF THE DRAWINGS

The above and/or other features will become apparent and more readily appreciated from the following description of example embodiments, taken in conjunction with the accompanying drawings of which.

DETAILED DESCRIPTION

Figure 1:
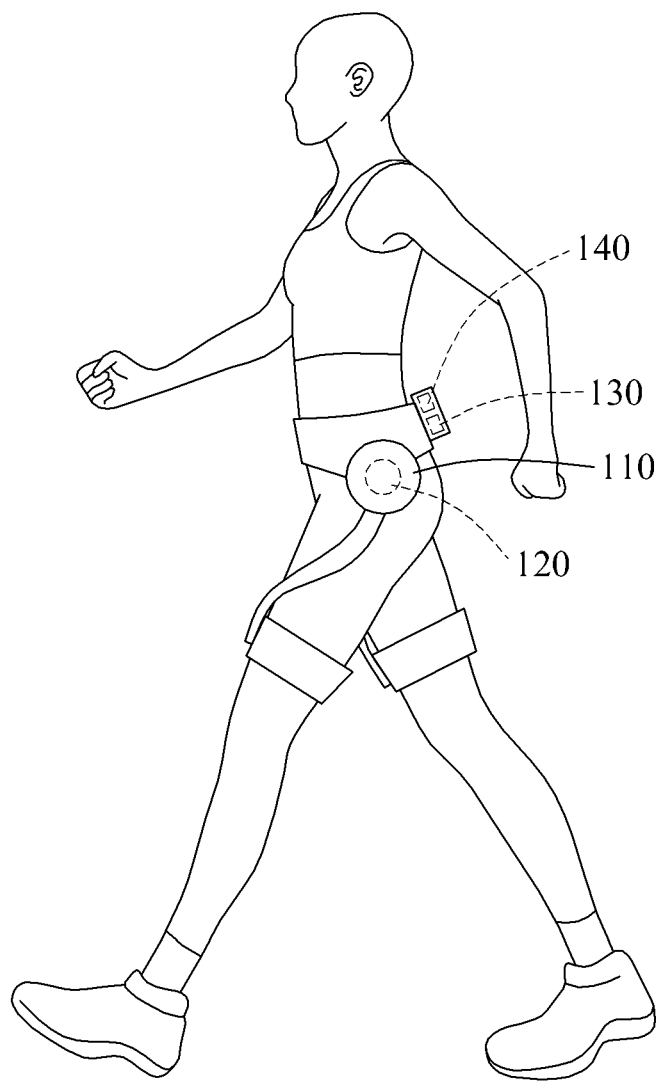
FIG. 1 illustrates a user wearing a walking assistance apparatus according to an example embodiment.

Reference will now be made in detail with reference to various example embodiments, examples of which are illustrated in the accompanying drawings, wherein like reference numerals refer to like elements throughout. Some example embodiments are described below to explain the present disclosure by referring to the figures.

In the drawings, the thicknesses of layers and regions are exaggerated for clarity. Like reference numerals in the drawings denote like elements.

Some detailed illustrative example embodiments are disclosed herein. However, specific structural and functional details disclosed herein are merely representative for purposes of describing the example embodiments. Example embodiments may be embodied in many alternate forms and should not be construed as limited to only those set forth herein.

It should be understood that there is no intent to limit this disclosure to the particular example embodiments disclosed herein. On the contrary, the example embodiments described herein are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown.

FIG. 1 illustrates a user wearing a walking assistance apparatus according to example embodiments.

Referring to FIG. 1, the walking assistance apparatus includes a driving portion 110, a sensor portion 120, an inertial measurement unit (IMU) sensor 130, and a controller 140. Although FIG. 1 illustrates a hip-type walking assistance apparatus, the type of the walking assistance apparatus is not limited thereto. The walking assistance apparatus may be applicable to, for example, a walking assistance apparatus that supports an entire pelvic limb, a walking assistance apparatus that supports a portion of a pelvic limb, etc. The walking assistance apparatus that supports a portion of a pelvic limb may be applicable to, for example, a walking assistance apparatus that supports up to a knee, a walking assistance apparatus that supports up to an ankle, etc.

The driving portion 110 may be disposed on, for example, each of a right hip portion and a left hip portion of a user to drive both hip joints of the user. The sensor portion 120 may measure both hip joint angle information of the user while the user is walking. Herein, the both hip joint angle information may also be referred to as right and left hip joint angle information. The sensor portion 120 may be disposed in the driving portion 110. The both hip joint angle information sensed by the sensor portion 120 may include at least one of angles of both hip joints, a difference between the angles of both hip joints, and motion directions of both hip joints.

The IMU sensor 130 may measure acceleration information and posture information while the user is walking. A landing point in time of a foot of the user may be detected based on the acceleration information measured by the IMU sensor 130. However, when a sensor capable of detecting a landing point in time of a foot is included in the walking assistance apparatus, the IMU sensor 130 may not be provided to recognize a gait motion.

The controller 140 may infer a gait motion of the user based on right and left hip joint angle information sensed at the detected landing point in time of the foot of the user, and detect a landing leg based on the inferred gait motion.

The gait motion of the user recognized by the controller 140 may include, for example, a level walking motion, a walking motion in an upward inclined direction, a walking motion in a downward inclined direction, and a standing motion.

As described above, human walking is performed using different operating mechanisms of hip joints for level walking, walking in an upward inclined direction (e.g., walking up stairs), and walking in a downward inclined direction (e.g., walking down stairs).

The controller 140 may recognize the gait motion of the user as described above, and output a control signal to control the driving portion 110 based on at least one of the inferred gait motion and the detected landing leg. The driving portion 110 may drive the hip joints of the user suitably for the recognized gait motion based on the control signal output from the controller 140.

Hereinafter, an apparatus for recognizing a gait motion included in the controller 140, and a method thereof will be described.

Figure 2:
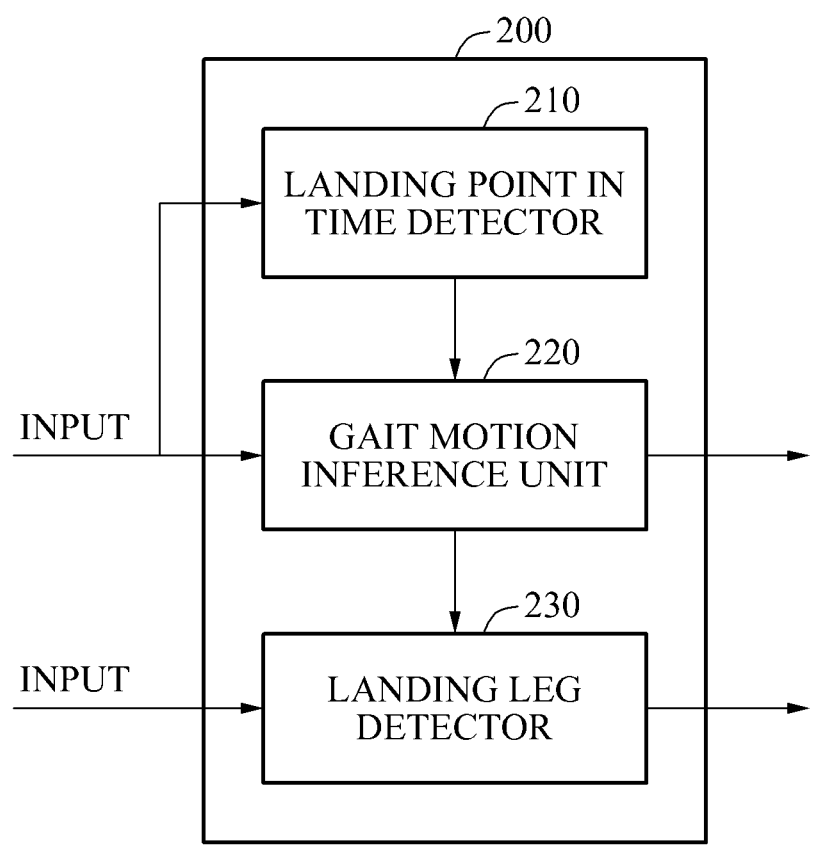
FIG. 2 shows a block diagram of an apparatus for recognizing a gait motion according to an example embodiment.

FIG. 2 shows a block diagram of an apparatus 200 for recognizing a gait motion according to an example embodiment.

Referring to FIG. 2, the apparatus 200 for recognizing a gait motion includes a landing point in time detector 210, a gait motion inference unit 220, and a landing leg detector 230.

The landing point in time detector 210 may detect a landing point in time of a foot of a user based on acceleration information sensed by the IMU sensor 130 of FIG. 1 or a separate acceleration sensor (not shown). For example, in the event that a walking assistance apparatus that supports an entire pelvic limb of a user may include a foot force sensor configured to detect a landing point in time of a foot of the user, the landing point in time detector 210 may detect a landing point in time of a foot of a user based on acceleration information sensed by the foot force sensor.

In the walking assistance apparatus that supports an entire pelvic limb, the foot force sensor may be provided on a bottom of a shoe to easily detect a landing point in time. In this example, the landing point in time detector 210 may not be included in the walking assistance apparatus. However, a walking assistance apparatus that supports a portion of a pelvic limb may not include a foot force sensor configured to detect a landing point in time of a foot of a user. In such cases, the landing point in time of the foot of the user is to be detected separately.

The landing point in time detector 210 may detect the landing point in time of the foot of the user based on the acceleration information sensed by the IMU sensor 130 or the acceleration sensor. The acceleration information may be, for example, a vertical acceleration, or a sum of squares of accelerations in an x-axial direction, a y-axial direction, and a z-axial direction corresponding to a vertical direction.

The landing point in time detector 210 may detect a prediction horizon as the landing point in time when a difference between a mean acceleration for a base horizon set based on a previous step duration horizon and a mean acceleration for the prediction horizon is greater than or equal to a threshold value.

The base horizon may refer to a horizon in which a landing point in time does not occur in the previous step duration horizon. The base horizon may be set to follow a freeze horizon preset from a landing point in time after a previous landing point in time occurs. The base horizon may be set to be uniform for each step, or may be updated for each step based on a previous base horizon.

The mean acceleration for the base horizon may also be updated for each step, or may be predetermined to be a uniform value as desired. As described above, the base horizon and the mean acceleration for the base horizon may be preset based on a general gait motion of a human. However, to detect a landing point in time more precisely based on characteristics of each user, the base horizon and the mean acceleration for the base horizon may be updated for each step.

The prediction horizon may start after a freeze horizon and a base horizon occur subsequent to the previous landing point in time. This reflects that a desired (or alternatively, predetermined) time is required between a current landing point in time and a subsequent landing point in time during human walking. Thus, the prediction horizon may be minimized. Further, detection of the landing point in time may be attempted in a horizon with a relatively high landing point in time detection probability. Thus, a detection performance may increase.

The landing point in time detector 210 may detect the landing point in time of the foot of the user by shifting the prediction horizon when the difference between the mean acceleration for the base horizon and the mean acceleration for the prediction horizon is less than the threshold value. As described above, the prediction horizon may be set to be a horizon with a relatively high landing point in time detection probability. However, a horizon in which a landing point in time is detected for each step of the user may be non-uniform depending on a walking condition for the user.

Thus, the landing point in time may not be detected in the prediction horizon set to follow the base horizon. When the difference between the mean acceleration for the base horizon and the mean acceleration for the prediction horizon is less than the threshold value, it may be determined that landing does not occur in the prediction horizon.

In this example, the landing point in time detector 210 may shift the prediction horizon, and compare the mean acceleration for the base horizon to a mean acceleration for the shifted prediction horizon. A method of the landing point in time detector 210 detecting the landing point in time of the foot of the user will be described later with reference to FIG. 3.

The gait motion inference unit 220 may infer a gait motion based on right and left hip joint angle information of the user sensed at the landing point in time of the foot of the user. The gait motion inference unit 220 may infer the gait motion of the user based on right and left hip joint angle information at a single step point in time of the user.

The gait motion inference unit 220 may infer the gait motion using a fuzzy logic. The gait motion inference unit 220 may infer the gait motion of the user based on, for example, angles of both hip joints of the user at the landing point in time of the foot of the user, a difference between the angles of both hip joints of the user, and motion directions of both hip joints of the user.

The gait motion of the user may be inferred by comparing the both hip joint angle information of the user to a threshold value, or through a separately preset rule. However, because each user has different walking characteristics and a walking condition for each user can be non-uniform, it may be difficult to infer a gait motion of a user accurately by simply setting a threshold value or using a set rule.

However, when a fuzzy logic is used, inference with a relatively intuitive and robust expression may be possible in comparison to the conventional threshold value based or set rule based method described above. According to some example embodiments, the gait motion inference unit 220 may receive the right and left hip joint angle information of the user, and infer the gait motion of the user through fuzzification and defuzzification of the received right and left hip joint angle information.

For example, the gait motion inference unit 220 may infer the gait motion of the user by performing defuzzification based on a desired (or alternatively, preset) fuzzy rule and a value obtained by fuzzification of the received right and left hip joint angle information using a membership function. The membership function may be set based on the right and left hip joint angle information.

The fuzzy rule may be "IF-THEN" rules which are set based on both hip joint angle information for, for example, a level walking motion, a walking motion in an upward inclined direction, a walking motion in a downward inclined direction, and a standing motion.

A process of inferring the gait motion of the user based on the right and left hip joint angle information will be described later with reference to FIG. 4.

The landing leg detector 230 may detect a landing leg between both legs of the user based on the gait motion inferred by the gait motion inference unit 220. For the walking assistance apparatus to assist walking of the user, the landing leg may be detected.

The landing leg detector 230 may detect the landing leg using different methods depending on the inferred gait motion. When the inferred gait motion corresponds to the level walking motion or the walking motion in the upward inclined direction, the landing leg detector 230 may detect, as the landing leg, a leg having a greater hip joint angle between angles of the right hip joint and the left hip joint.

When the inferred gait motion corresponds to the walking motion in the downward inclined direction, the landing leg detector 230 may detect, as the landing leg, a leg having a motion direction with a negative velocity between motion directions of the right hip joint and the left hip joint.

In view of the both hip joint angle information, the landing leg detector 230 may set a method of detecting the landing leg differently for the gait motion inferred by the gait motion inference unit 220. A method of detecting the landing leg using the landing leg detector 230 will be described later with reference to FIGS. 5 through 7.

As described above, the gait motion recognized by the apparatus 200 for recognizing a gait motion may be applied as information to be used by the walking assistance apparatus to provide a user with a walking assistance optimized for each gait motion.

Figure 3:
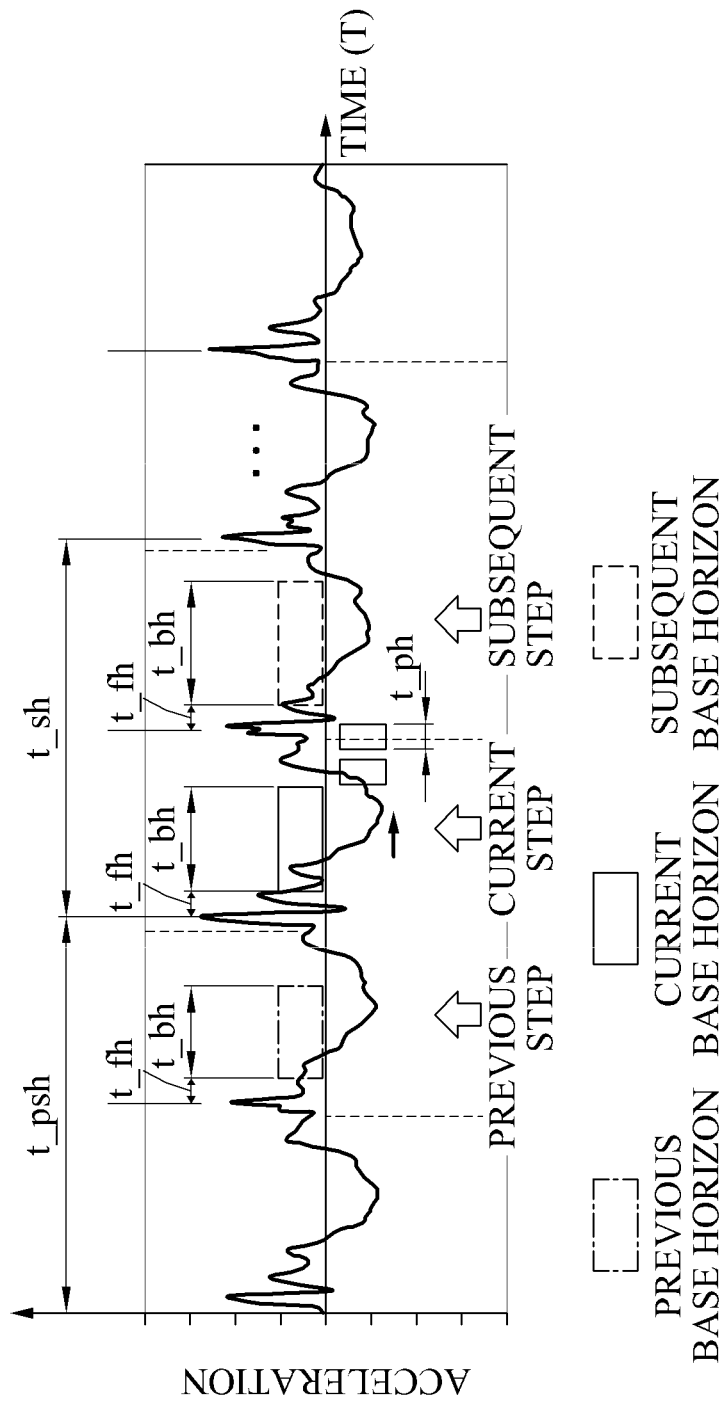
FIG. 3 illustrates a sensed acceleration and horizons to be used to detect a landing point in time according to an example embodiment.

FIG. 3 illustrates a sensed acceleration and horizons to be used to detect a landing point in time according to an example embodiment.

FIG. 3 is a graph illustrating a relationship between a time and an acceleration sensed by the IMU sensor 130 of FIG. 1 or an acceleration sensor. In the graph, t_psh denotes a previous stride horizon, and t_sh denotes a current stride horizon. t_bh denotes a base horizon, t_fh denotes a freeze horizon, and t_ph denotes a prediction horizon.

The base horizon may be a horizon in which a landing point in time does not occur in a previous step duration horizon. The base horizon may be set to be uniform for each step, or may be updated for each step based on a previous base horizon.

The base horizon may be set to follow the freeze horizon preset from a previous landing point in time to prevent or mitigate an error in detection of the landing point in time after the landing point in time is detected. Taking into account that a time period is required between the landing point in time and a subsequent landing point in time, the prediction horizon may be set to follow the base horizon.

A method of detecting a landing point in time of a subsequent step based on a current step using the landing point in time detector 210 will be described. A horizon for the current step may be estimated using a horizon for a previous step. When a landing point in time of the current step is detected, a desired freeze horizon may be set from the landing point in time. As described above, the freeze horizon may be a horizon set or preset to prevent or mitigate an error in detection of the landing point in time.

To detect the landing point in time of the subsequent step, a mean acceleration for the base horizon may be compared to a mean acceleration for a prediction horizon. The freeze horizon set or preset to prevent or mitigate an error in detection of the landing point in time may be set to accurately set the mean acceleration for the base horizon estimated to be a horizon in which a landing point in time does not occur.

The current base horizon may be set based on a step duration horizon for the previous step. The horizon for the current step may be estimated based on the previous step duration horizon, and the base horizon may be set based on the estimated horizon for the current step.

For example, in detection of the landing point in time of the current step from the previous step, a difference between a mean acceleration for a previous base horizon and a mean acceleration for an initially set prediction horizon may be less than a threshold value. In this example, the prediction horizon may be shifted to detect the landing point in time.

When a landing point in time is detected in the shifted prediction horizon, an actual duration horizon for the previous step estimated based on a step previous to the previous step may increase to an extent corresponding to a shifted portion of the prediction horizon. The horizon for the current step may be set based on the actual duration horizon for the previous step. Thus, the current base horizon may be updated to a horizon obtained by adding the shifted portion of the prediction horizon to the previous base horizon.

The prediction horizon may be shifted and set to follow the freeze horizon and the base horizon after the landing point in time of the current step occurs. The prediction horizon may be set or preset to minimize the prediction horizon and to allow the difference between the mean acceleration for the base horizon and the mean acceleration for the prediction horizon to be greater than or equal to the threshold value when the landing point in time occurs.

When the difference between the mean acceleration for the base horizon and the mean acceleration for the prediction horizon is greater than or equal to the threshold value, the landing point in time detector 210 may detect the prediction horizon as the landing point in time. For example, a point in time at which acceleration is maximized in the prediction horizon may be detected as the landing point in time.

When the difference between the mean acceleration for the base horizon and the mean acceleration for the prediction horizon is less than the threshold value, the landing point in time detector 210 may determine that landing of the foot of the user does not occur in the prediction horizon.

In this example, the landing point in time detector 210 may shift the prediction horizon, and compare a difference between the mean acceleration for the base horizon and a mean acceleration for the shifted prediction horizon to the threshold value. The landing point in time detector 210 may detect the landing point in time by shifting the prediction horizon until the difference between the mean acceleration for the base horizon and the mean acceleration for the prediction horizon is greater than or equal to the threshold value.

When the landing point in time of the subsequent step is detected, the landing point in time detector 210 may store a final step duration horizon corresponding to an actual duration horizon for the current step. By storing the final step duration horizon for the current step, the landing point in time detector 210 may estimate a horizon for the subsequent step.

When a landing point in time of a step subsequent to the subsequent step is to be detected, a duration horizon for the subsequent step may be estimated through the stored final step duration horizon for the current step. Further, a subsequent base horizon may also be updated based on the base horizon for the current step and the prediction horizon in which the landing point in time is detected.

As described above, the base horizon and the mean acceleration for the base horizon may be updated for each step. While the user is walking, a step duration horizon and an acceleration may be non-uniform. Thus, a current base horizon and a mean acceleration for the current base horizon may be updated for each step through a previous step duration horizon.

However, when a step duration horizon and an acceleration of a user do not have large deviations for each step, the base horizon and the mean acceleration for the base horizon may be set to be uniform values, thereby reducing a computational complexity of the landing point in time detector 210.

As described above, in a walking assistance apparatus not including a foot force sensor, a landing point in time may be detected through the landing point in time detector 210. The landing point in time detected through the landing point in time detector 210 may be provided to the gait motion inference unit 220. The gait motion inference unit 220 may infer a gait motion based on both hip joint angle information of the user at the provided landing point in time.

Figure 4:
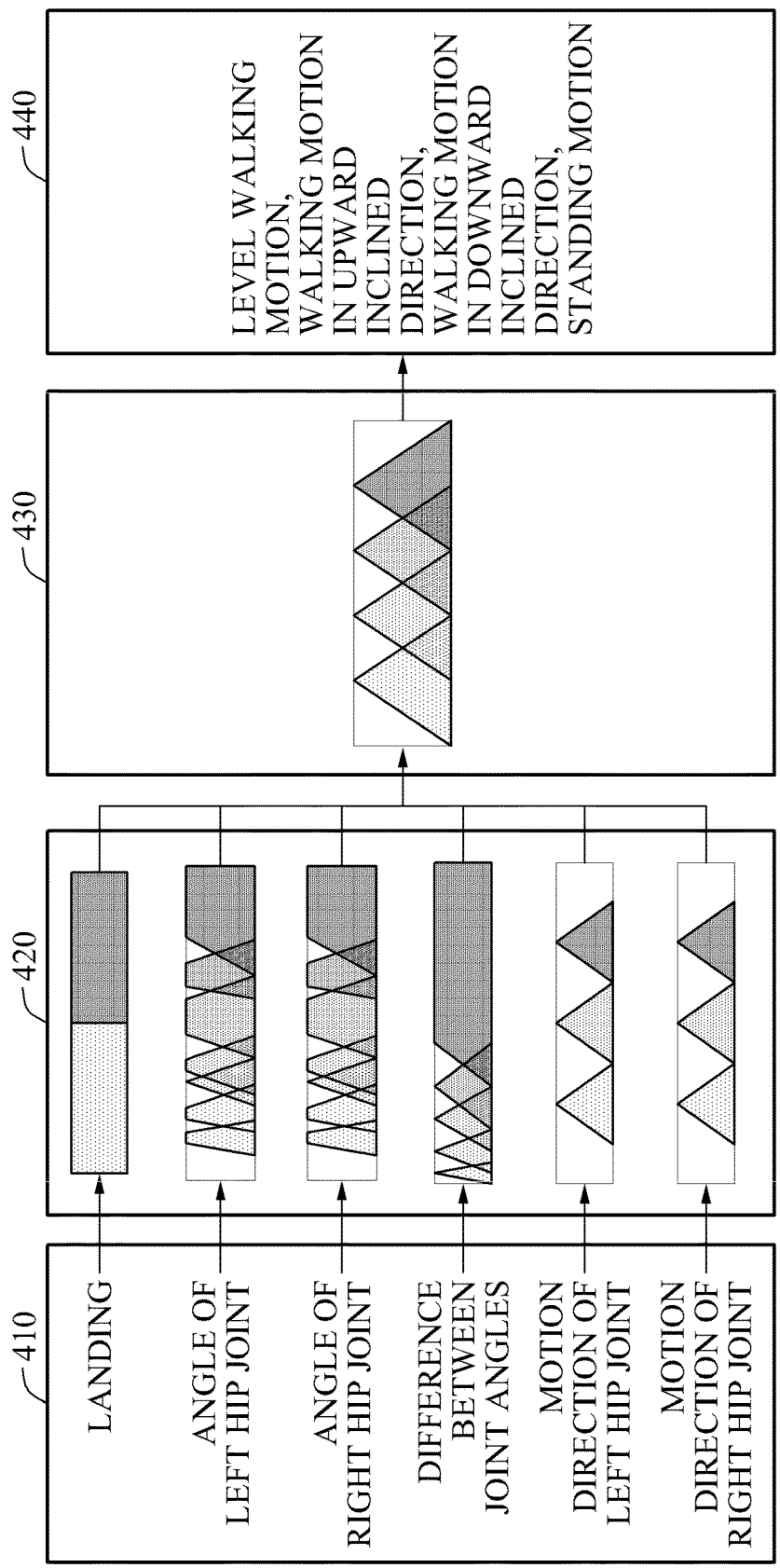
FIG. 4 illustrates a process of inferring a gait motion using a fuzzy logic according to an example embodiment.

FIG. 4 illustrates a process of inferring a gait motion using a fuzzy logic according to an example embodiment.

Referring to FIG. 4, an input 410 includes a landing point in time and both hip joint angle information to be input into the gait motion inference unit 220. The input 410 includes, as an input parameter, at least one of a landing point in time, an angle of a left hip joint, an angle of a right hip joint, a difference between the angles of both hip joints, a motion direction of the left hip joint, and a motion direction of the right hip joint.

A member function may be set or preset for each input 410 to be provided to the gait motion inference unit 220. The member function may be set or preset based on a characteristic of each input parameter included in the input 410.

For example, a member function set for the angle of the left hip joint, among the input parameters, may be classified into ranges of NEMID, NELOW, ZERO, POLOW, POMID, POHIGH, and POVHIGH based on the angle of the left hip joint, and expressed as a membership function. The membership function may indicate a degree of a value of an input parameter belonging to a classified range based on the value of the input parameter.

Similar to the angle of the left hip joint, a member function corresponding to each of the input parameters may be classified into ranges and expressed as a membership function. However, the foregoing is provided as an example for ease of description, and may be set differently based on a characteristic of each input parameter and a characteristic of a user.

The gait motion inference unit 220 may perform fuzzification 420 on a value of each input parameter through a member function corresponding to each input parameter. The gait motion inference unit 220 may obtain a fuzzified value of each input parameter by performing the fuzzification 420 on each input parameter through the member function.

The fuzzification 420 may correspond to a process of calculating a degree of the value of each input parameter belonging to each range classified in a member function corresponding to each input parameter. For example, when the angle of the left hip joint is 20°, an input angle of the left hip joint belonging to POLOW by 0.5 and POMID by 0.5 may be expressed by the fuzzified value.

The gait motion inference unit 220 may perform defuzzification 430 based on a set or preset fuzzy rule and the value obtained by the fuzzification 420 of each input parameter using the member function. For example, the fuzzy rule may be "IF-THEN" rules which are set or preset based on both hip joint angle information for a level walking motion, a walking motion in an upward inclined direction, a walking motion in a downward inclined direction, and a standing motion.

For example, the fuzzy rule may be defined as "IF-THEN" rules as follows.

1. rule: if FootStrike is ON and LeftHipAng is POVHIGH and RightHipAng is POLOW and AbsHipAngDiff is HIGH then WalkMode is STAIRUP
2. rule: if FootStrike is ON and LeftHipAng is POVHIGH and RightHipAng is ZERO and AbsHipAngDiff is HIGH then WalkMode is STAIRUP
3. rule: if FootStrike is ON and LeftHipAng is POMID and RightHipAng is POMID and AbsHipAngDiff is VLOW then WalkMode is STAIRDOWN
4. rule: if FootStrike is ON and LeftHipAng is POMID and RightHipAng is POMID and AbsHipAngDiff is LOW then WalkMode is STAIRDOWN
5. rule: if FootStrike is ON and LeftHipAng is POHIGH and RightHipAng is NELOW and AbsHipAngDiff is HIGH then WalkMode is LEVEL
6. rule: if FootStrike is ON and LeftHipAng is POHIGH and RightHipAng is NEMID and AbsHipAngDiff is VHIGH then WalkMode is LEVEL Rules 1 through 6 may be included in a single fuzzy rule, and may be a fuzzy rule to be used to infer a gait motion based on each input parameter.

Rule 1 is a rule in which, when a landing point in time is detected, an angle of a left hip joint belongs to POVHIGH, an angle of a right hip joint belongs to POLOW, and a difference between the angles of both hip joints belongs to HIGH, a gait motion is inferred as a walking motion in an upward inclined direction.

Rule 2 is a rule in which, when a landing point in time is detected, an angle of a left hip joint belongs to POVHIGH, an angle of a right hip joint belongs to ZERO, and a difference between the angles of both hip joints belongs to HIGH, a gait motion is inferred as a walking motion in an upward inclined direction.

Rule 3 is a rule in which, when a landing point in time is detected, an angle of a left hip joint belongs to POMID, an angle of a right hip joint belongs to POMID, and a difference between the angles of both hip joints belongs to HIGH, a gait motion is inferred as a walking motion in a downward inclined direction.

Rule 4 is a rule in which, when a landing point in time is detected, an angle of a left hip joint belongs to POMID, an angle of a right hip joint belongs to POMID, and a difference between the angles of both hip joints belongs to LOW, a gait motion is inferred as a walking motion in a downward inclined direction.

Rule 5 is a rule in which, when a landing point in time is detected, an angle of a left hip joint belongs to POHIGH, an angle of a right hip joint belongs to NELOW, and a difference between the angles of both hip joints belongs to HIGH, a gait motion is inferred as a level walking motion.

Rule 6 is a rule in which, when a landing point in time is detected, an angle of a left hip joint belongs to POHIGH, an angle of a right hip joint belongs to NEMID, and a difference between the angles of both hip joints belongs to VHIGH, a gait motion is inferred as a level walking motion.

However, the "IF-THEN" rules are provided as an example for ease of description. It is obvious to those skilled in the art that the rules may be set differently depending on a characteristic of a gait motion.

As described above, the gait motion inference unit 220 may infer a gait motion of a user by performing the defuzzification 430 based on the fuzzy rule, a range to which each input parameter belongs, and the value obtained by the fuzzification 420 of each input parameter using the member function.

The gait motion inference unit 220 may output results 440 of finally inferring the gait motion through the defuzzification 430. The results 440 of inferring the gait motion may be classified into, for example, a level walking motion, a walking motion in an upward inclined direction, a walking motion in a downward inclined direction, and a standing motion, and may be output.

A fuzzy logic is one example of artificial intelligence technologies for performing deductive inference based on a fuzzy rule. The gait motion inference unit 220 may infer the gait motion of the user using the fuzzy logic, thereby inferring the gait motion of the user with a relatively intuitive and robust expression in comparison to a method using a simple threshold value and/or combination of rules.

Figure 5:
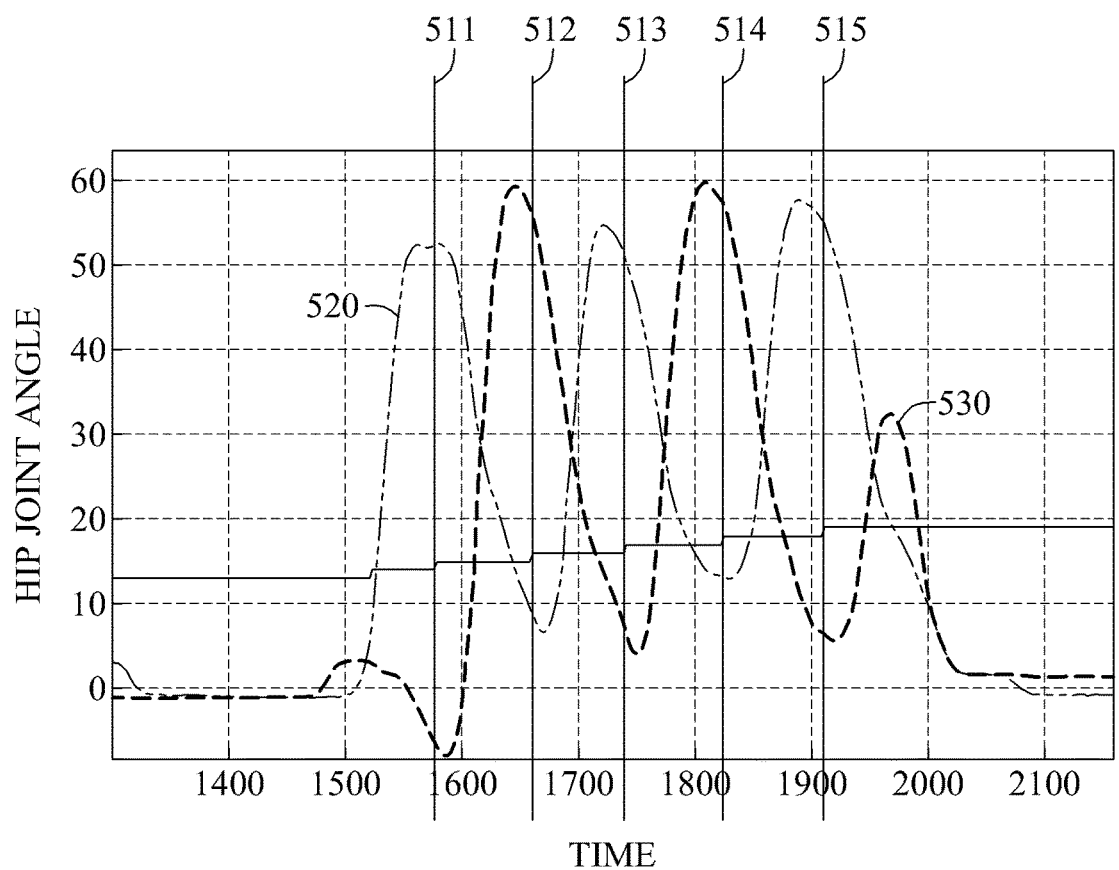
FIG. 5 illustrates trajectories of angles of both hip joints of a user for a walking motion in an upward inclined direction according to an example embodiment.

FIG. 5 illustrates trajectories of angles of both hip joints of a user for a walking motion in an upward inclined direction according to an example embodiment.

Referring to FIG. 5, a graph illustrating a trajectory 520 of an angle of a right hip joint of a user and a trajectory 530 of an angle of a left hip joint of the user for a walking motion in an upward inclined direction is provided. In the graph, an x axis denotes a time, and a y axis denotes a hip joint angle.

When a gait motion inferred by the gait motion inference unit 220 corresponds to a walking motion in an upward inclined direction, the landing leg detector 230 may detect, as a landing leg, a leg having a greater hip joint angle between the angles of the right hip joint and the left hip joint.

Considering the trajectories 520, 530 of angles of both hip joints for a walking motion in an upward inclined direction shown in FIG. 5, the landing leg detector 230 may detect, as the landing leg, a leg having a greater hip joint angle between the angles of the right hip joint and the left hip joint at each landing point in time 511, 512, 513, 514, or 515.

Based on the foregoing description, the landing leg at each landing point in time 511, 512, 513, 514, or 515 may be detected as follows. At the landing points in time 511, 513, and 515, a right leg may be detected as the landing leg because the angle of the right hip joint is greater than the angle of the left hip joint. At the landing points in time 512 and 514, a left leg may be detected as the landing leg because the angle of the left hip joint is greater than the angle of the right hip joint.

Figure 6:
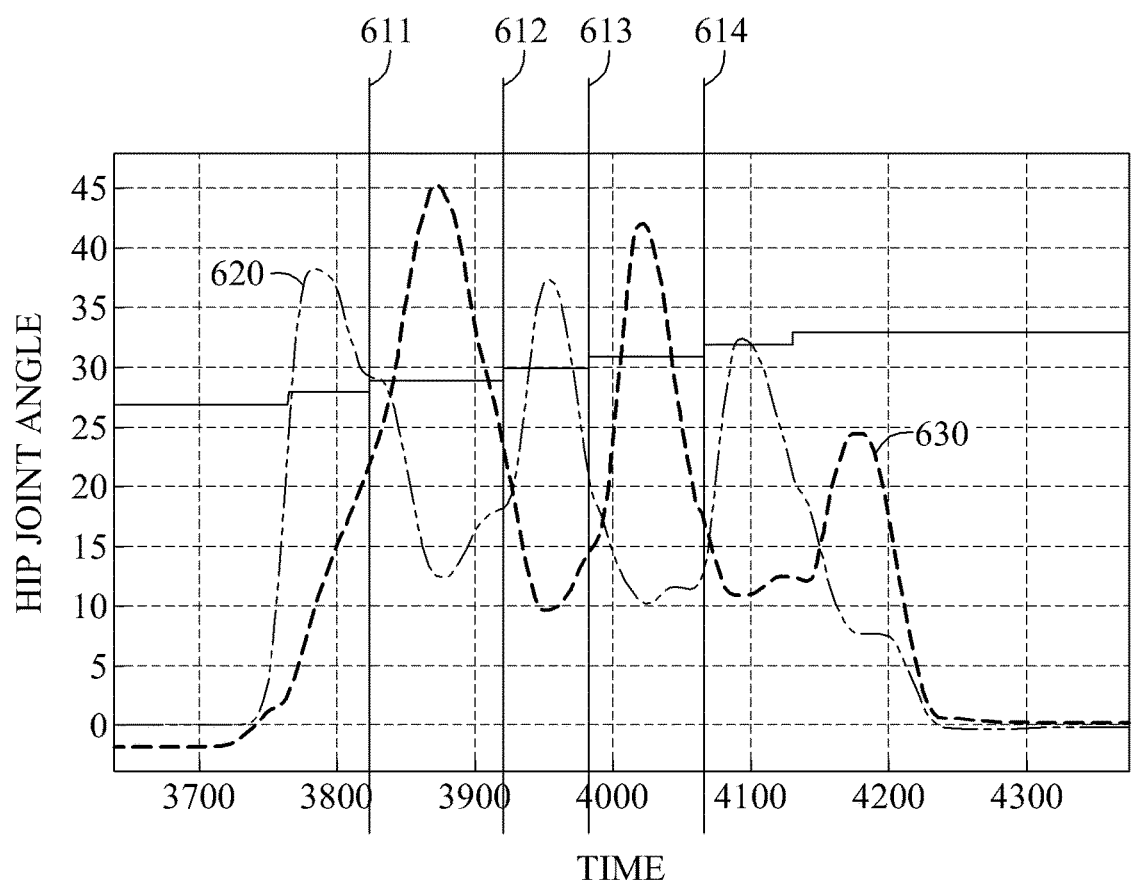
FIG. 6 illustrates trajectories of angles of both hip joints of a user for a walking motion in a downward inclined direction according to an example embodiment.

FIG. 6 illustrates trajectories of angles of both hip joints of a user for a walking motion in a downward inclined direction according to an example embodiment.

Referring to FIG. 6, a graph illustrating a trajectory 620 of an angle of a right hip joint of a user and a trajectory 630 of an angle of a left hip joint of the user for a walking motion in a downward inclined direction are provided. In the graph, an x axis denotes a time, and a y axis denotes a hip joint angle.

When a gait motion inferred by the gait motion inference unit 220 corresponds to a walking motion in a downward inclined direction, the landing leg detector 230 may detect, as a landing leg, a leg having a motion direction with a negative velocity between motion directions of the right hip joint and the left hip joint.

Considering the trajectories of angles 620, 630 of both hip joints for a walking motion in a downward inclined direction shown in FIG. 6, the landing leg detector 230 may detect, as the landing leg, a leg having a motion direction with a negative velocity between the motion directions of the right hip joint and the left hip joint at each landing point in time 611, 612, 613, or 614.

Based on the foregoing description, the landing leg at each landing point in time 611, 612, 613, or 614 may be detected as follows. At the landing points in time 611 and 613, a right leg may be detected as the landing leg because the motion direction of the right hip joint has a negative velocity. At the landing points in time 612 and 614, a left leg may be detected as the landing leg because the motion direction of the left hip joint has a negative velocity.

Figure 7:
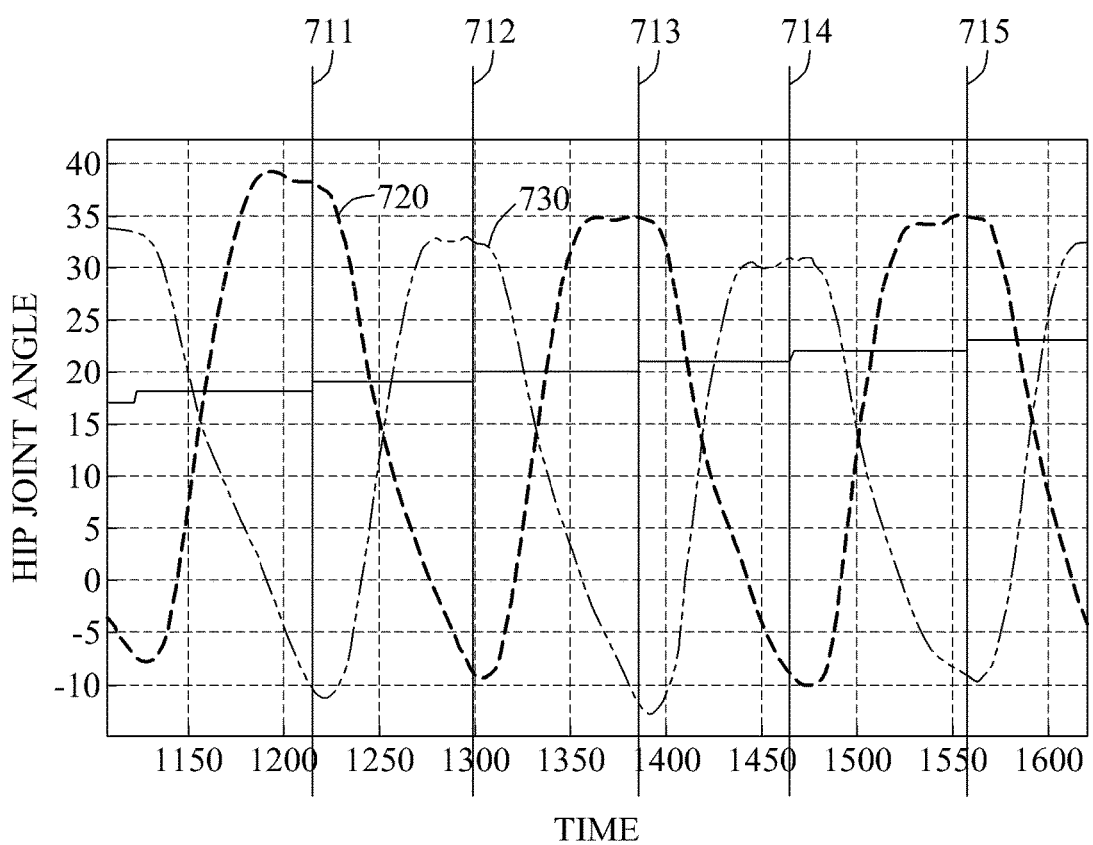
FIG. 7 illustrates trajectories of angles of both hip joints of a user for a level walking motion according to an example embodiment.

FIG. 7 illustrates trajectories of angles of both hip joints of a user for a level walking motion according to an example embodiment.

Referring to FIG. 7, a graph illustrating a trajectory 720 of an angle of a right hip joint of a user and a trajectory 730 of an angle of a left hip joint of the user for a level walking motion is provided. In the graph, an x axis denotes a time, and a y axis denotes a hip joint angle.

When a gait motion inferred by the gait motion inference unit 220 corresponds to a level walking motion, the landing leg detector 230 may detect, as a landing leg, a leg having a greater hip joint angle between the angles of the right hip joint and the left hip joint.

Considering the trajectories 720, 730 of angles of both hip joints for a level walking motion shown in FIG. 7, the landing leg detector 230 may detect, as the landing leg, a leg having a greater hip joint angle between the angles of the right hip joint and a left hip joint at each landing point in time 711, 712, 713, 714, or 715.

Based on the foregoing description, the landing leg at each landing point in time 711, 712, 713, 714, or 715 may be detected as follows. At the landing points in time 711, 713, and 715, a left leg may be detected as the landing leg because the angle of the left hip joint is greater than the angle of the right hip joint. At the landing points in time 712 and 714, a right leg may be detected as the landing leg because the angle of the right hip joint is greater than the angle of the left hip joint.

As described with reference to FIGS. 5 through 7, the landing leg detector 230 may detect a landing leg based on different criteria for a gait motion inferred by the gait motion inference unit 220.

Figure 8:
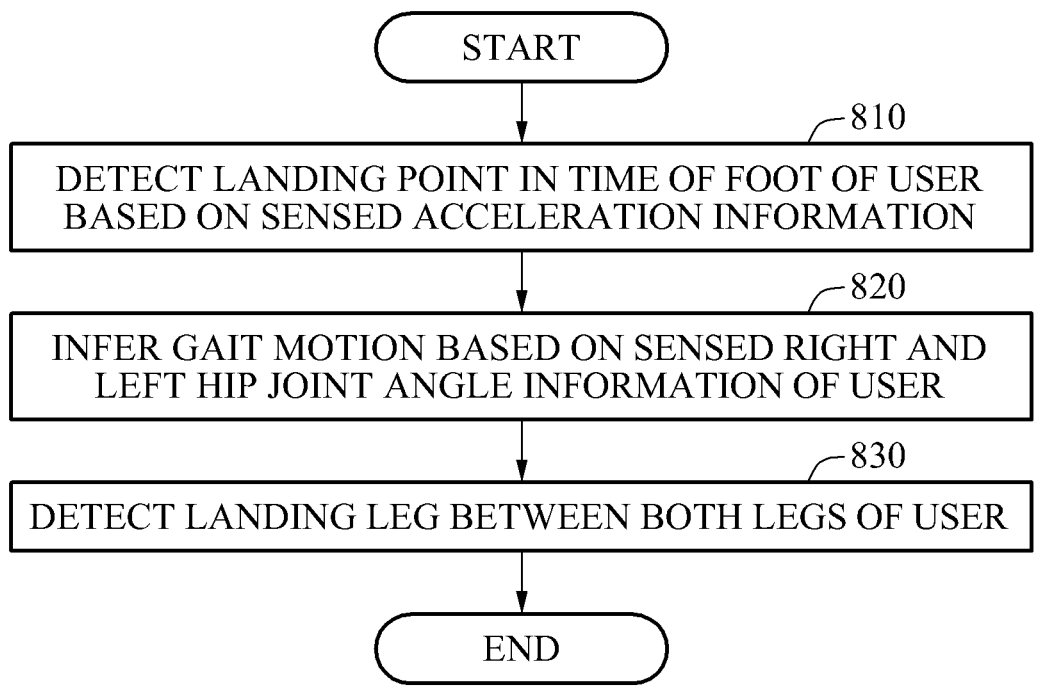
FIG. 8 shows a flow chart illustrating a method of recognizing a gait motion according to an example embodiment.

FIG. 8 shows a flow chart illustrating a method of recognizing a gait motion according to an example embodiment.

Referring to FIG. 8, in operation 810, the landing point in time detector 210 of FIG. 2 may detect a landing point in time of a foot of a user based on acceleration information sensed by the IMU sensor 130 of FIG. 1 or a separate acceleration sensor. The landing point in time detector 210 may detect a prediction horizon as the landing point in time when a difference between a mean acceleration for a base horizon set based on a previous step duration horizon and a mean acceleration for the prediction horizon is greater than or equal to a threshold value.

The landing point in time detector 210 may detect the landing point in time of the foot of the user by shifting the prediction horizon when the difference between the mean acceleration for the base horizon and the mean acceleration for the prediction horizon is less than the threshold value.

In operation 820, the gait motion inference unit 220 of FIG. 2 may infer a gait motion based on right and left hip joint angle information of the user sensed at the landing point in time of the foot of the user. The gait motion inference unit 220 may infer the gait motion of the user based on right and left hip joint angle information at a single step point in time of the user.

The gait motion inference unit 220 may infer the gait motion using a fuzzy logic. The gait motion inference unit 220 may infer the gait motion of the user based on, for example, angles of both hip joints of the user at the landing point in time of the foot of the user, a difference between the angles of both hip joints of the user, and motion directions of both hip joints of the user.

The gait motion inference unit 220 may infer the gait motion of the user by performing defuzzification based on a preset fuzzy rule and a value obtained by fuzzification of the right and left hip joint angle information using a member function. The member function may be set based on the right and left hip joint angle information.

In operation 830, the landing leg detector 230 of FIG. 2 may detect a landing leg between both legs of the user based on the gait motion inferred by the gait motion inference unit 220.

When the gait motion inferred by the gait motion inference unit 220 corresponds to a level walking motion or a walking motion in an upward inclined direction, the landing leg detector 230 may detect, as the landing leg, a leg having a greater hip joint angle between angles of a right hip joint and a left hip joint.

When the gait motion inferred by the gait motion inference unit 220 corresponds to a walking motion in a downward inclined direction, the landing leg detector 230 may detect, as the landing leg, a leg having a motion direction with a negative velocity between motion directions of the right hip joint and the left hip joint.

Figure 9:
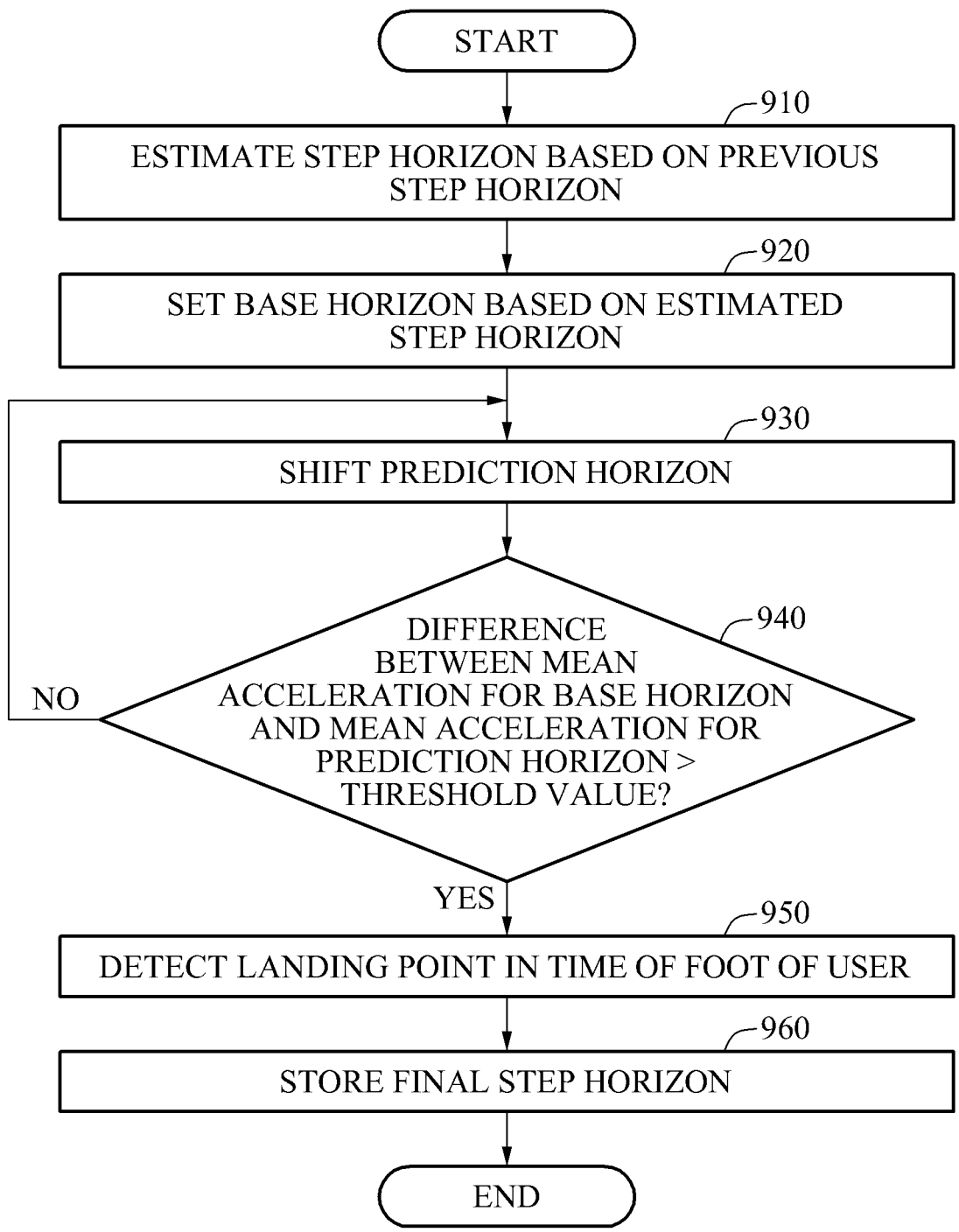
FIG. 9 shows a flow chart illustrating a method of detecting a landing point in time according to an example embodiment.

FIG. 9 shows a flow chart illustrating a method of detecting a landing point in time according to an example embodiment.

Referring to FIG. 9, in operation 910, the landing point in time detector 210 of FIG. 2 may estimate a horizon for a current step based on a horizon for a previous step. The horizon for the current step may be estimated based on the horizon for the previous step considering that a horizon for each step may not differ greatly.

In operation 920, the landing point in time detector 210 may set a base horizon based on the estimated horizon for the current step. The base horizon may be a horizon in which a landing point in time does not occur in a previous step duration horizon. The base horizon may be set to be uniform for each step, or may be updated for each step based on a previous base horizon.

In operation 930, the landing point in time detector 210 may shift a prediction horizon to be set to follow a freeze horizon and the base horizon after a landing point in time of the current step occurs. The prediction horizon may be set or preset to minimize the prediction horizon and to allow a difference between a mean acceleration for the base horizon and a mean acceleration for the prediction horizon to be greater than or equal to a threshold value when the landing point in time occurs.

In operation 940, the landing point in time detector 210 may compare the difference between the mean acceleration for the base horizon and the mean acceleration for the prediction horizon to the threshold value. The threshold value is a desired (or alternatively, preset) value, and a reference value to be used to determine whether the landing point in time occurs based on the difference between the mean accelerations.

When the difference between the mean acceleration for the base horizon and the mean acceleration for the prediction horizon is less than the threshold value, the landing point in time detector 210 may determine that landing of a foot of the user does not occur in the prediction horizon. In this example, the landing point in time detector 210 may shift the prediction horizon, and compare a difference between the mean acceleration for the base horizon and a mean acceleration for the shifted prediction horizon to the threshold value.

In operation 950, when the difference between the mean acceleration for the base horizon and the mean acceleration for the prediction horizon is greater than or equal to the threshold value, the landing point in time detector 210 may detect the prediction horizon as the landing point in time. For example, a point in time at which an acceleration is maximized in the prediction horizon may be detected as the landing point in time.

In operation 960, when a landing point in time of a subsequent step is detected, the landing point in time detector 210 may store a final step duration horizon corresponding to an actual duration horizon for the current step. By storing the final step duration horizon for the current step, the landing point in time detector 210 may estimate a horizon for the subsequent step.

The portion, units and/or modules described herein may be implemented using hardware components and software components. For example, the hardware components may include microphones, amplifiers, band-pass filters, audio to digital convertors, and processing devices. A processing device (e.g., controller) may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for recognizing a gait motion, the apparatus comprising:
   at least one sensor configured to sense acceleration information and right and left hip joint angle information of a user;

a controller configured to,
  detect a landing point in time of a foot of the user based on the sensed acceleration information, the landing point in time is a time point at which a foot of the user lands, and further detect a prediction horizon as the landing point in time when a difference between a mean acceleration for a base horizon set based on a previous step duration horizon and a mean acceleration for the prediction horizon is greater than or equal to a threshold value,
  infer a gait motion based on the sensed right and left hip joint angle information of the user, the right and left hip joint angle information sensed at the landing point in time,
  detect a landing leg between both legs of the user based on the inferred gait motion, and
  output a control signal based on at least one of the inferred gait motion and the detected landing leg; and
a driver configured to drive a hip joint of the user based on the control signal.

2. The apparatus of claim 1, wherein the sensed right and left hip joint angle information comprises at least one of angles of a right hip joint and a left hip joint, a difference between the angles of the right hip joint and the left hip joint, and motion directions of the right hip joint and the left hip joint.

3. The apparatus of claim 1, wherein the gait motion comprises a level walking motion, a walking motion in an upward inclined direction, a walking motion in a downward inclined direction, and a standing motion.

4. The apparatus of claim 1, wherein the base horizon is set to follow a freeze horizon set from a previous landing point in time.

5. The apparatus of claim 1, wherein the controller is further configured to detect the landing point in time of the foot of the user by shifting the prediction horizon when the difference between the mean acceleration for the base horizon and the mean acceleration for the prediction horizon is less than the threshold value.

6. The apparatus of claim 1, wherein the controller is further configured to infer the gait motion using a fuzzy logic.

7. The apparatus of claim 6, wherein the controller is further configured to infer the gait motion by performing defuzzification based on a fuzzy rule and a value obtained by fuzzification of the sensed right and left hip joint angle information using a member function, and
  the member function is set based on the sensed right and left hip joint angle information.

8. The apparatus of claim 1, wherein the controller is further configured to detect, as the landing leg, a leg having a greater hip joint angle between angles of the right hip joint and the left hip joint included in the sensed right and left hip joint angle information when the inferred gait motion corresponds to a level walking motion or a walking motion in an upward inclined direction.

9. The apparatus of claim 1, wherein the controller is further configured to detect, as the landing leg, a leg having a motion direction with a negative velocity between motion directions of the right hip joint and the left hip joint included in the sensed right and left hip joint angle information when the inferred gait motion corresponds to a walking motion in a downward inclined direction.

10. A walking assistance apparatus comprising:
a driving mechanism configured to drive a right hip joint and a left hip joint of a user;
a sensor configured to sense right and left hip joint angle information;
an inertial measurement unit (IMU) sensor configured to sense acceleration information in response to walking of the user; and
a controller configured to
  detect a landing point in time of a foot of the user based on the sensed acceleration information,
  infer a gait motion of the user based on the right and left hip joint angle information of the user sensed at the detected landing point in time of the foot of the user,
  detect a landing leg based on the inferred gait motion, and
  control the driving mechanism based on at least one of the inferred gait motion of the user and the detected landing leg,
wherein the controller is further configured to detect a prediction horizon as the landing point in time when a difference between a mean acceleration for a base horizon set based on a previous step duration horizon and a mean acceleration for the prediction horizon is greater than or equal to a threshold value.

11. The apparatus of claim 10, wherein the controller is further configured to infer the gait motion using a fuzzy logic.

12. The apparatus of claim 10, wherein the controller is further configured to:
detect, as the landing leg, a leg having a greater hip joint angle between angles of the right hip joint and the left hip joint included in the sensed right and left hip joint angle information when the inferred gait motion corresponds to a level walking motion or a walking motion in an upward inclined direction, and
detect, as the landing leg, a leg having a motion direction with a negative velocity between motion directions of the right hip joint and the left hip joint included in the sensed right and left hip joint angle information when the inferred gait motion corresponds to a walking motion in a downward inclined direction.

13. A method of recognizing a gait motion, the method comprising:
sensing, by at least one sensor, acceleration information of a user;
detecting, by a controller, a landing point in time of a foot of a user based on the sensed acceleration information;
sensing, by the at least one sensor, right and left hip joint angle information of the user at the detected landing point in time of the foot of the user;
inferring, by the controller, a gait motion based on the sensed right and left hip joint angle information of the user;
detecting, by the controller, a landing leg between both legs of the user based on the inferred gait motion;
outputting a control signal based on at least one of the inferred gait motion and the detected landing leg; and
driving a hip joint of the user based on the control signal,
wherein the detecting a landing point in time includes detecting a prediction horizon as the landing point in time when a difference between a mean acceleration for a base horizon set based on a previous step duration horizon and a mean acceleration for the prediction horizon is greater than or equal to a threshold value.

14. The method of claim 13, wherein the inferring comprises inferring the gait motion by performing defuzzification based on a fuzzy rule and a value obtained by fuzzification of the sensed right and left hip joint angle information using a member function, and the member function is set based on the sensed right and left hip joint angle information.

15. The method of claim 13, wherein the detecting a landing leg comprises:
   detecting, as the landing leg, a leg having a greater hip joint angle between angles of a right hip joint and a left hip joint included in the sensed right and left hip joint angle information when the inferred gait motion corresponds to a level walking motion or a walking motion in an upward inclined direction; and
   detecting, as the landing leg, a leg having a motion direction with a negative velocity between motion directions of the right hip joint and the left hip joint included in the sensed right and left hip joint angle information when the inferred gait motion corresponds to a walking motion in a downward inclined direction.

* * * * *